(12) United States Patent
Zhou et al.

(10) Patent No.: US 11,901,047 B2
(45) Date of Patent: Feb. 13, 2024

(54) MEDICAL VISUAL QUESTION ANSWERING

(71) Applicant: International Business Machines Corporation, Armonk, NY (US)

(72) Inventors: Yuan Zhou, Beijing (CN); Jing Mei, Beijing (CN); Shiwan Zhao, Beijing (CN); Yi Qin Yu, Beijing (CN); Xu Min, Beijing (CN); Yan Fei Wang, Shanghai (CN)

(73) Assignee: International Business Machines Corporation, Armonk, NY (US)

( * ) Notice: Subject to any disclaimer, the term of this patent is extended or adjusted under 35 U.S.C. 154(b) by 738 days.

(21) Appl. No.: 17/082,334

(22) Filed: Oct. 28, 2020

(65) Prior Publication Data

US 2022/0130499 A1  Apr. 28, 2022

(51) Int. Cl.
*G06T 11/00* (2006.01)
*G16H 10/20* (2018.01)
(Continued)

(52) U.S. Cl.
CPC .......... *G16H 10/20* (2018.01); *A61B 6/5217* (2013.01); *G06F 16/538* (2019.01); *G06F 18/213* (2023.01); *G06F 18/214* (2023.01); *G06F 40/205* (2020.01); *G06F 40/284* (2020.01); *G06F 40/30* (2020.01); *G06N 3/04* (2013.01); *G06T 11/00* (2013.01); *G06V 10/40* (2022.01); *G16H 30/20* (2018.01); *G16H 30/40* (2018.01); *G16H 50/20* (2018.01); *G16H 50/70* (2018.01); *A61B 5/0077* (2013.01); *A61B 6/032* (2013.01); *G06T 2210/12* (2013.01); *G06V 2201/03* (2022.01)

(58) Field of Classification Search
CPC ..... G06F 16/538; G06V 10/40; A61B 6/5217; G06N 30/04; G06T 11/00
See application file for complete search history.

(56) References Cited

U.S. PATENT DOCUMENTS

2017/0140240 A1* 5/2017 Socher .................. G06F 18/254
2020/0042819 A1* 2/2020 Zhang .................... G06N 3/006
(Continued)

FOREIGN PATENT DOCUMENTS

WO      2019211250 A1    11/2019

OTHER PUBLICATIONS

Anonymous, "Method and System for Enabling Semantic Grounded Visual Question Answering." IPCOM, Apr. 12, 2019. 2 Pages.
(Continued)

*Primary Examiner* — Edward Park
(74) *Attorney, Agent, or Firm* — CANTOR COLBURN LLP; Michael A. Petrocelli

(57) ABSTRACT

Aspects of the invention include a computer-implemented method including extracting a domain-specific object feature from a first image data, wherein the feature describes an object in the first image data. A domain-specific semantic meaning of text data is determined. The object feature is mapped to a portion of the text data, wherein the portion of the text data describes the object. A joint representation of the object and the portion of the text data is created. A second image data and a query directed towards an object in the second image data is received. An answer to the query is generated based on the joint representation.

20 Claims, 9 Drawing Sheets

(51) Int. Cl.
*G16H 30/40* (2018.01)
*G16H 50/70* (2018.01)
*G16H 50/20* (2018.01)
*G06F 16/538* (2019.01)
*G06N 3/04* (2023.01)
*G06F 40/30* (2020.01)
*G06F 40/205* (2020.01)
*G06F 40/284* (2020.01)
*A61B 6/00* (2006.01)
*G16H 30/20* (2018.01)
*G06V 10/40* (2022.01)
*G06F 18/213* (2023.01)
*G06F 18/214* (2023.01)
*A61B 6/03* (2006.01)
*A61B 5/00* (2006.01)

(56) References Cited

U.S. PATENT DOCUMENTS

| | | | | |
|---|---|---|---|---|
| 2020/0177942 A1* | 6/2020 | Wu | | G06F 16/3347 |
| 2020/0293921 A1* | 9/2020 | Huang | | G06F 16/5846 |
| 2021/0012102 A1* | 1/2021 | Cristescu | | G06F 40/284 |
| 2021/0021949 A1* | 1/2021 | Sridharan | | H04R 5/04 |
| 2021/0056353 A1* | 2/2021 | Vahdat | | G06V 10/761 |
| 2022/0130499 A1* | 4/2022 | Zhou | | G06T 11/60 |
| 2023/0281400 A1* | 9/2023 | Wang | | G06F 40/284 704/2 |

OTHER PUBLICATIONS

Lau et al., "A dataset of clinically generated visual questions and answers about radiology images." www.nature.com/scientificdata, Nov. 20, 2018. 10 Pages.

Shi et al., "Deep Multimodal Learning for Medical Visual QuestionAnswering." CEUR-WS.org/vol. 2380, Sep. 12, 2019. 8 Pages.

Yu et al., "Multi-level Attention Networks for Visual Question Answering." IEEE Conference, Jul. 26, 2017, 9 Pages.

* cited by examiner

MEDICAL VISUAL QUESTION ANSWERING

BACKGROUND

The present invention generally relates to programmable computing systems, and more specifically, to programmable computers configured and arranged to perform medical visual question answering.

Computer-based visual question answering systems can receive a digital image and provide a response to a question about the image. A visual question answering system can be tasked with analyzing the question and searching for objects in the image related to the question. Therefore, the computer visual question answering system has to analyze the questions in relation to the content of the digital image. As such, computer visual question answering is a complex process that involves textual analysis and visual analysis to determine an image and text relationship through computer-based reasoning.

SUMMARY

Embodiments of the present invention are directed to visual question answering. A non-limiting example computer-implemented method includes extracting a domain-specific object feature from a first image data, wherein the feature describes an object in the first image data. A domain-specific semantic meaning of text data is determined. The object feature is mapped to a portion of the text data, wherein the portion of the text data describes the object. A joint representation of the object and the portion of the text data is created. A second image data and a query directed towards an object in the second image data is received. An answer to the query is generated based on the joint representation.

Other embodiments of the present invention implement features of the above-described method in computer systems and computer program products.

Additional technical features and benefits are realized through the techniques of the present invention. Embodiments and aspects of the invention are described in detail herein and are considered a part of the claimed subject matter. For a better understanding, refer to the detailed description and to the drawings.

BRIEF DESCRIPTION OF THE DRAWINGS

The specifics of the exclusive rights described herein are particularly pointed out and distinctly claimed in the claims at the conclusion of the specification. The foregoing and other features and advantages of the embodiments of the invention are apparent from the following detailed description taken in conjunction with the accompanying drawings in which:

Figure 1:
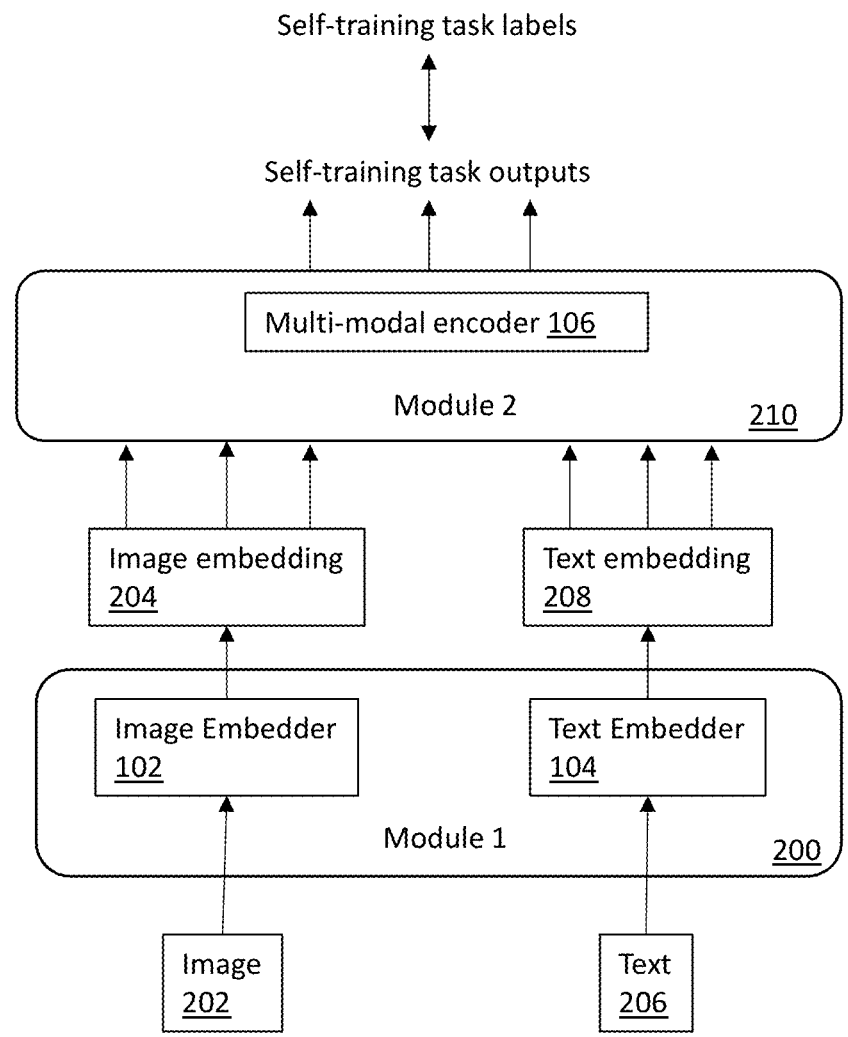
FIG. 1 illustrates a training phase for a visual question answering system in accordance with one or more embodiments of the present invention.

The diagrams depicted herein are illustrative. There can be many variations to the diagrams or the operations described therein without departing from the spirit of the invention. For instance, the actions can be performed in a differing order, or actions can be added, deleted, or modified. Also, the term "coupled" and variations thereof describes having a communications path between two elements and does not imply a direct connection between the elements with no intervening elements/connections between them. All of these variations are considered a part of the specification.

DETAILED DESCRIPTION

One or more embodiments of the present invention provide computer-implemented methods, computing systems, and computer program products for training a visual question answering system to generate a joint representation of information received from different formats. The joint representation describes a relationship between the information, which can be used to generate an answer to a query about an image.

Healthcare professionals and patients are increasingly communicating via healthcare portals and internet-enabled video conferencing. These new lines of communication and the ability to digitally store medical records has enabled healthcare patients and medical students to have greater access to medical imaging data. In each of these situations, the patients or the students may have basic questions about the images, but limited access to healthcare professionals. The patients and students can turn to visual question answering (VQA) systems. However, the accuracy of answers generated by conventional VQA systems is limited by the size of the dataset used to recognize objects in a target image. Conventional VQA systems generate inaccurate answers at a higher frequency because they are trained with small training datasets. This is due to the unavailability of large datasets for training VQA systems in the healthcare space. Furthermore, in conventional VQA systems, the systems are trained using image training data concatenated with textual training data. Concatenating the data leads to losing information regarding the relationship of the image and the text.

One or more embodiments of the present invention address one or more of the above-described shortcomings by providing computer-implemented methods, computing systems, and computer program products for a VQA system that includes an encoder that is trained using medical imaging data and medical records. The herein described VQA system can combine data presented via multiple modalities into a joint representation of all of the data. The joint representation is based on a mapping between the data derived from medical records and data derived from medical images. The herein described VQA system further includes a decoder that is decoupled from the encoder, and therefore does not require additional medical records or images for training the encoder. The decoupling reduces the need for large-scale image-question-answering data. Rather, small-scale data can be used for training the decoder (i.e., image query data with answer labels). This is because the joint representation pre-trained in a first training phase using medical records and medical images keeps a strong representation across the dual modalities.

Referring to FIGS. 1, 2, 3, and 4, a multi-phase process of training a VQA system 100 is described. As seen in FIG. 1, a first phase of the training is illustrated. The first phase is executed on a first module 200, which includes an image embedder unit 102 and a text embedder unit 104. The image embedder unit 102 is operable to receive an image 202 as a training instance and employ a model to identify objects in the image 202. The image 202 can be, for example, an x-ray image, a CT scan, a photographic image, or other medically related image data. The image embedder unit 102 can employ a model that executes computer vision techniques on the image 202 for object detection. Object detection includes both image classification and object localization. Image classification includes predicting a class of one or more objects in the image 202. To perform image classification, the image embedder unit 102 receives the image 202 as an input and outputs a class label in the form of one or more integer values mapped to class values. Object localization includes identifying a location of the one or more identified objects in the image 202. To perform object localization, the image embedder unit 102 can process the received image 202 and output one or more bounding boxes, which define a spatial relationship of the objects in the image 202. The image embedder unit 102 can be implemented through a neural network type architecture with input, hidden, and output layers. The image embedder unit 102 can be trained to detect objects from a particular domain (e.g., medical domain) by adjusting the weights and biases of the neural network. The image embedder unit 102 further uses the values of the weights and biases to generate an image embedding vector 204 to represent the identified objects. The weights control the signal between two neurons of a neural network. A weight determines the extent an input dictates an output. Biases are constants that are an additional input into the next layer of a neural network. Biases not determined by a previous layer of a neural network. Therefore, even if an output of a previous layer is zero, the bias ensures that an input will be entered into a subsequent layer.

An exemplary embodiment, the image embedder unit 102 employs a trained artificial neural network to execute the model, for example, a region-based convolutional neural network (R-CNN), or other neural network appropriate for image analysis. The R-CNN generally operates in three phases. First, the R-CNN analyzes the image 202, extracts independent regions in the image 202, and delineates the regions as candidate bounding boxes. Second, the R-CNN extracts features, for example, using a deep convolutional neural network, from each region. Third, a classifier, for example, a support vector machine (SVM), is used to analyze the features and predict a class for one or more objects in a region.

The text embedder unit 104 can receive a text document 206 in electronic form as a training instance and derive a semantic meaning of the document. The text document 206 can be an electronic medical record, physician's notes, journal article or other textual document. The text document 206 describes at least a portion of the image 202. For example, the text document 206 can be a transcription of a physician's impressions of an x-ray, where the x-ray is the image 202. The text embedder unit 104 can apply natural language processing techniques, via a model, to semantically analyze the text document 206. The model can be, for example, a word embedding model. The text embedder unit 104 can receive the text document 206 and segment it into passages (e.g., paragraphs, sections, etc.). The text embedder unit 104 can further segment the passages into tokens (e.g., words and phrases). The text embedder unit 104 can retrieve individual passages and map the tokens in the passage to respective words vectors in a low-dimensional space. Various techniques can be applied to derive a context of the text document 206. For example, the text embedder unit 104 can take a target word for the embedding being learned and attempt to predict the surrounding context words from it. In another embodiment of the present invention, the text embedder unit 104 analyzes the context of the words surrounding a masked target word and seeks to predict the target word based on the surrounding words. The text embedder unit 104 can be implemented through a neural network type architecture with input, hidden, and output layers. The text embedder unit 104 can be trained to semantically analyze text from a particular domain (e.g., medical domain) by adjusting the weights and biases of the neural network. The text embedder unit 104 further uses the values of the weights and biases to generate a text embedding vector 208 to represent the semantic meaning of the text document 206.

In some embodiments of the present invention, the text embedder unit 104 can apply machine learning techniques to perform the semantic analysis. In an exemplary embodiment, the text embedder unit 104 employs a trained artificial neural network, for example, a recurrent neural network (RNN), or other neural network appropriate for text analysis.

The image embedding vectors 204 and the text embedding vectors 208 are high-dimensional vectors that can be translated in a low-dimensional embedding space. By representing the objects by the embedding vectors in the low-dimensional space, the system 100 can combine the information generated from different modalities, even if the vectors have different dimensions. For example, the image 202 includes a large amount of information describing pixel features. On the other hand, the text document 306 includes a relatively smaller amount of information related to the semantic meaning. By converting both the image 202 and the text document 206 into respective embedding vectors 204 208 within the same embedding space, the system 100 can map the image embedding vector 204 text embedding vector 208, regardless of the dimensional differences.

The image embedder unit 102 and the text embedder unit 104 can transmit the image embedding vector 204 and the text embedding vector 208 to the second module 210, which includes a multi-modal encoder 212. It should be appreciated that although the herein described figures describe two modalities, image and text, the first module 200 is operable to receive data from more than two modalities. For example, in some embodiments of the present invention, the first module 200 can receive auditory data, such as a microphone recording. Furthermore, the two described modalities are described as images and text for illustration purposes. In some embodiments of the present invention, the two modalities can include image data and audio data, rather than image data and text data.

Figure 2A:
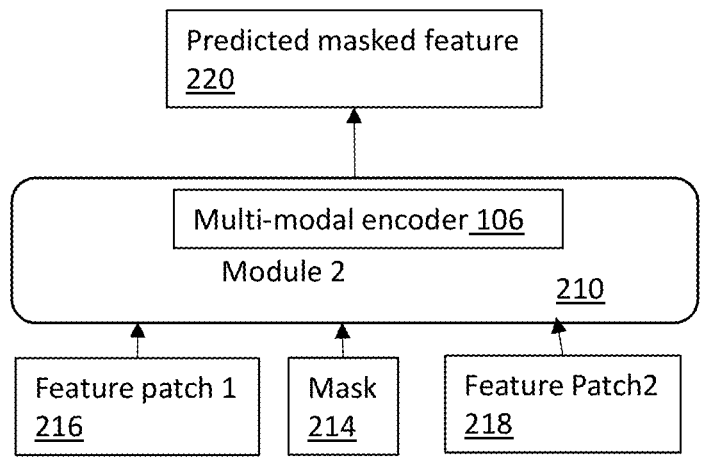
FIG. 2A illustrates a training phase for object detection for a visual question answer system in accordance with one or more embodiments of the present invention.
Figure 2B:
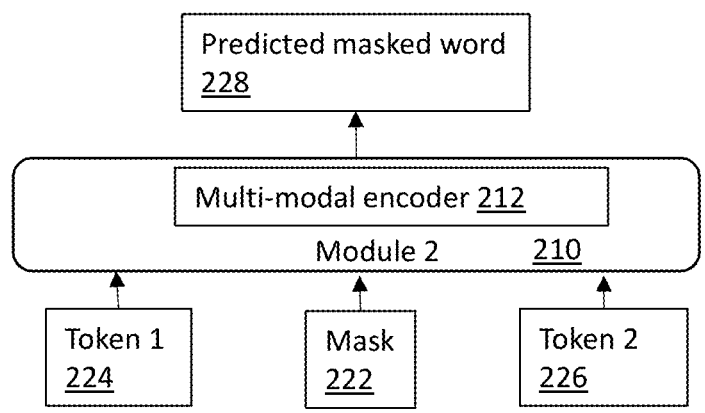
FIG. 2B illustrates a training phase for semantic analysis for a visual question answer system in accordance with one or more embodiments of the present invention.

Referring to FIGS. 2A and 2B, an illustration of the second phase of the pre-training is illustrated. The second phase includes training the second module 210 and permitting a trained second module 210 to make inferences. The second phase is performed by the second module 210 which learns features found the image embedding vector 204 that relate to features in the text embedding vector 208, and vice-versa. The second module 210 includes a multi-modal encoder 212 for encoding a relationship between features from the image embedding vector 204 and the text embedding vector 208. In some embodiments of the present invention, the multi-modal encoder 212 can be implemented as feed-forward artificial neural network, for example, a multi-layer perceptron.

Referring to FIG. 2A, the multi-modal encoder 212 can receive the image embedding vector 204 and be trained to recognize domain-specific features. Various methods can be used to recognize the features, for example, the multi-modal encoder 212 can employ masked feature model. In some embodiments of the present invention, the masked feature model is trained to recognize features of a particular domain, for example, the healthcare domain. This can be performed by adjusting the weights and biases of the neural network to recognize healthcare domain-specific features. The multi-modal encoder 212 can receive the image embedding vector 204 and employ the masked feature model to predict domain-specific features from the vector. The masked feature model can mask a feature such that it is not recognizable by subsequent layers of the neural network. The masked-layer model can receive the context features patches 216 218 surrounding the masked feature 214 as inputs to generate a predicted masked feature 220 as to what the masked feature 214 should be. It should be appreciated that although FIG. 3A only illustrate a first feature patch 216 and a second feature patch 218, in practice, the masked feature model can receive greater than two feature patches to make a prediction as to the masked feature 214.

Referring to FIG. 2B, the multi-modal encoder 212 can also receive the text embedding vector 208 and be trained to derive a meaning from the vector. Various methods can be used to derive a context of the words described by the text embedding vector 208, for example, the multi-modal encoder 212 can employ a masked language model. The multi-modal encoder 212 can receive the text embedding vector 208 and employ the masked language model to segment the vector to describe respective passages on the text document 206. Passages can include, for example, sentences, phrases, and bullet points. The masked language model masks a token such that it is not recognizable by subsequent layers of the neural network. The masked-layer model then uses the context tokens 224 226 surrounding the masked token 222 to generate a predicted masked token 228 as to what the masked token 222 should be. It should be appreciated that although FIG. 2B only illustrates a first token 224 and a second token 226, the masked feature model can receive greater than two tokens to make a prediction as to the masked token 222.

Figure 3:
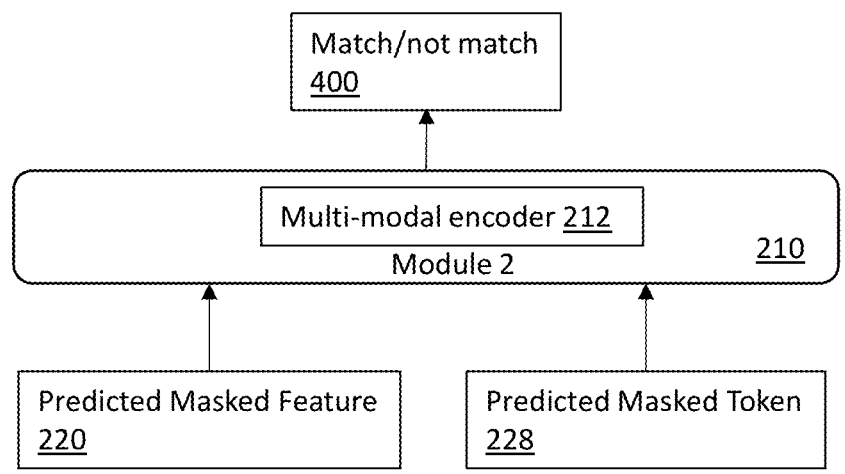
FIG. 3 illustrates a training phase for a visual question answering system in accordance with one or more embodiments of the present invention.

Referring to FIG. 3, the multi-modal encoder 212 can be trained to determine whether a relationship exists between the predicted masked feature 220 and the predicted masked token 228. In some embodiments of the present invention, the multi-model encoder 212 can employ an image-text matching model to determine the relationship between the predicted masked feature 220 and the predicted masked token 228. The image-text matching model can determine a semantic relationship between an object described in the image embedding vector 204 and the words described in the text embedding vector 208. The multi-modal encoder 212 can employ the image-text matching model to generate a nature language description of the objects in the image. As described above, the multi-modal encoder 212 can be trained to predict a word based on surrounding words, and predict a feature based on surrounding features. Therefore, the multi-modal encoder 212 can predict match based on a context of surrounding tokens and surrounding feature patches.

The multi-modal encoder 212 can employ an attention mechanism that allows the encoder to have the ability to focus on a subset of tokens (or features). The attention module mechanism can be implemented on a two-dimensional convolutional layer of a neural network, and include a sigmoid function to generate a mask of the feature map of the embedding space. The attention mechanism can receive an a×b×c feature map as an input and outputs a 1×b×c as an output attention map. The attention mechanism then performs an element-wise multiplication on the attention map with the input feature map to get a more refined and highlighted output.

The multi-modal encoder 212 can employ the image-text matching model to match features from the image embedding vector 204 and tokens from the text embedding vector 208. The image-text matching model can perform this function even though the image embedding vector 204 and text embedding vector 208 have different dimensions. The multi-modal encoder 212 can employ the image-text matching model to map the features and tokens into a same vector space and determine a match or not a match 400. The multi-modal encoder 212 can employ a classifier that is trained to determine whether an text matches an image or an object in an image. For example, if a token describes a liver and an image feature describes a liver, the classifier can be trained to determine a match exists. If, however, a token describes a broken arm and an image feature describes an ear, the classifier can be trained to determine that there is no match. The multi-modal encoder 212 can also employ the image-text matching model to generate pairs of tokens (or sets of tokens) and features (or sets of features) and determine a probability that the pairs are a match or not a match. A match suggests that the token or set of tokens describes the object described by a feature or set of features.

Figure 4:
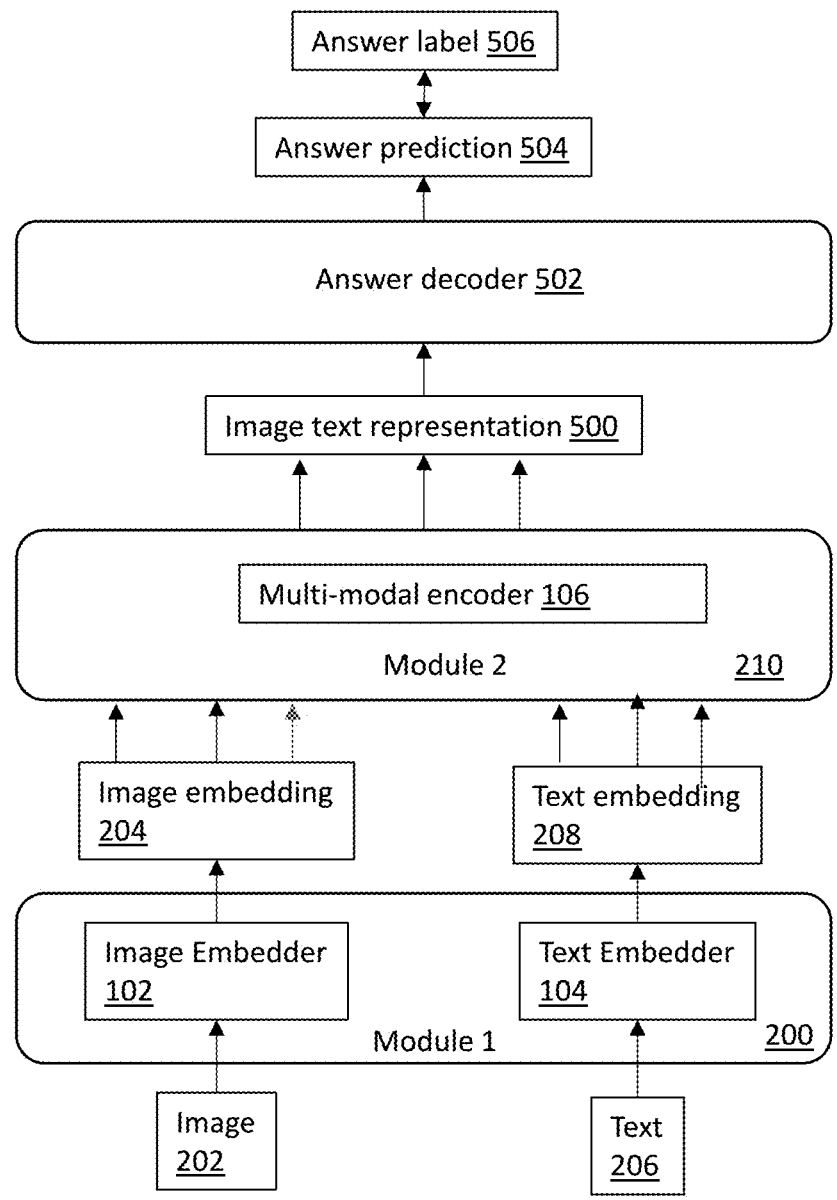
FIG. 4 illustrates a training phase for a visual question answering system in accordance with one or more embodiments of the present invention.

Referring to FIG. 4, a third phase of the pre-training is illustrated. The multi-modal encoder 212 can generate an image-text representation 500 in the form of a high dimensional vector. The image-text representation 500 is based on a matching of a token (or set of tokens) and an image feature (or set of image features). The matching features from the image embedding vector 204 are mapped to matching tokens from text embedding vector 208. The mapping is used to generate a joint image-text representation 500 describing a contextual representation of both image and text. Therefore, rather than concatenating an image embedding vector and a text embedding vector, the multi-modal encoder 212 generates a joint image-text representation 500 of the matching tokens and features.

Conventional concatenation is a simple and rough combination of image and text embeddings. The concatenated image and text embedding do not describe the relationship between image patches and the corresponding text tokens. All the images patches and text tokens share the same and uniform weights to generate the answer tokens, which leads to inaccurate answer generation. The herein described computer-implemented methods, computing systems, and computer program products use adaptive weights when generating the answer tokens. In detail, for a single step, an answer token is generated, the weights of different image patches and text tokens are different. For the next step when generating another answer token, the weights are changed adaptively. In other words, the weights assigned to different image patches, different text tokens, and different time step are all different. The weights can be referred to as the "attention vector/attention map", which quantifies how much the image-text matching model "pays attention to" each image patch and text token when generating an answer token. The attention weights are determined during the training of image-text matching model and lead to more accurate answer generation than conventional methods.

The third phase of the pre-training includes generating answers to queries. The multi-modal encoder 212 can transmit the image-text representation 500 to an answer decoder 502. The answer decoder 502 can receive a training query 112 and an image 110 as inputs and generate an answer prediction 504. The answer decoder 502 can be implemented by a neural network. The answer decoder 502 can further be in the form of a sequential generating model, such a long short-term memory (LTSM) or transformer decoder. An LSTM network is a form of a recurrent neural network (RNN) capable of learning order dependence in sequence prediction problem. A transformer decoder is another sequence learning neural network. The answer prediction 504 can be retrieved from a database 116 and provided in natural language. During the third training phase, a determination is made whether the answer prediction is correct or incorrect. The answer decoder 502 can be trained through supervised learning by matching an answer prediction 504 with an answer label 506 provided in a training set of answers. The answer decoder 502 can map a correct answer to an associated image-text representation 500.

In some embodiments of the present inventions, the encoding is decoupled from the decoding. The first module 200 is trained using images and text data that are readily available in large quantities. For example, medical images and medical records are readily available to form training instances. The first module 200 and the second module 210 are trained using the image and text training instances. However, answer decoder 502 receives the image-text representation 500, and therefore uses few training instances are needed than with conventional VQA systems due to foundation provided by the image-text representation 500. Therefore, the training process is less resource-intensive as the answer decoder 502 does not need its own set of training instances.

Figure 5:
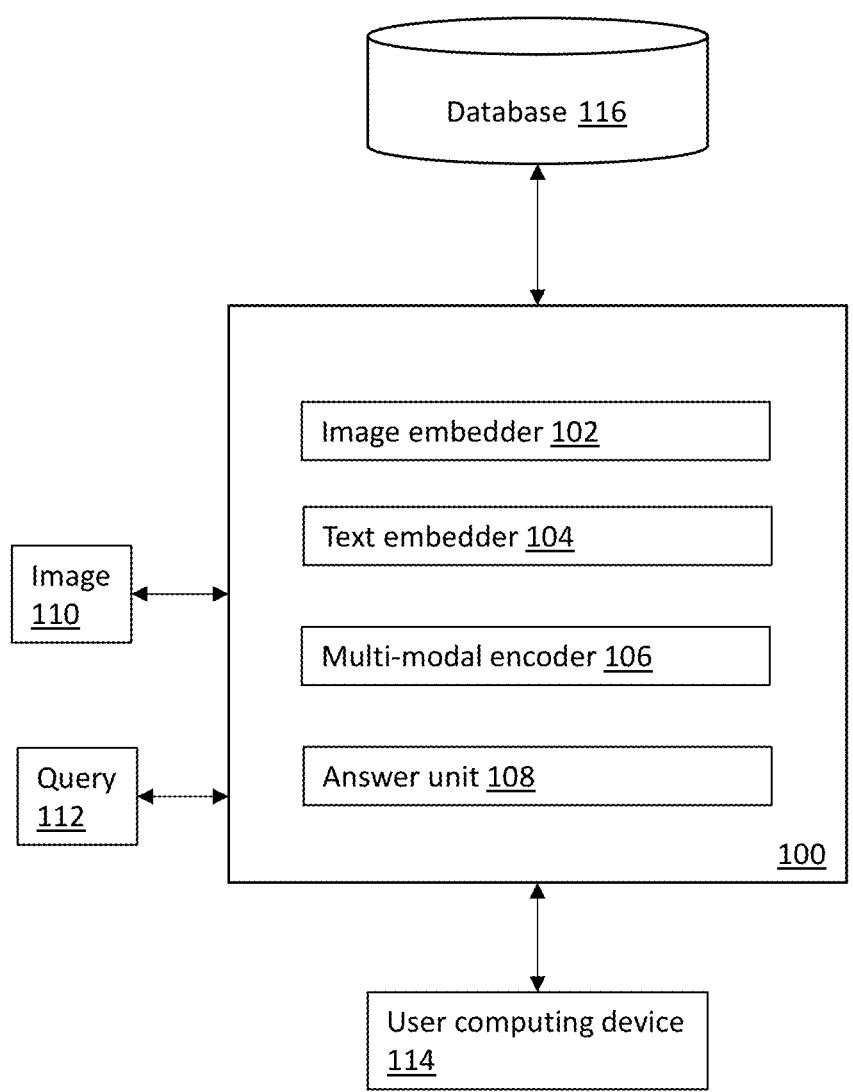
FIG. 5 illustrates a block diagram of components of a visual question answering system in accordance with one or more embodiments of the present invention.

Turning now to FIG. 5, a visual question answer system 100 is generally shown in accordance with one or more embodiments of the present invention. The system 100 includes a text embedder unit 104 for receiving a natural language text, for example, a search query from a user, and semantically analyzing the text. The system 100 further includes an image embedder unit 102 for analyzing an image and extracting features from objects in the image. The system 100 further includes a multi-modal encoder unit 106 for combining multiple embedding vectors into a single vector. The system 100 further includes an answer unit 108 for generating an answer to the query 112 that includes search query in relation to an image 110.

The image embedder unit 102 can receive an image 110 from and extract domain-specific features describing objects in the image 110. The image embedder unit 102 can further employ a computer vision model to detect and label domain specific-objects in the image 110. The image embedder unit 102 can receive the image 110 as an input and predict a class for each object contained in the image 110. The image embedder unit 102 can further label each object class. The image embedder unit 102 can generate a user image embedding vector to represent the extracted features and identified object classes.

The text embedder unit 104 is operable to receive a query 112 in electronic format from a user computing device 114. The query 112 can be a question from a user requesting information about some aspect of the image, for example, "What is the most alarming part in this x-ray scan?" The text embedder unit 104 can apply a model that uses natural language processing (NLP) techniques to analyze to query 112 and determine a context of the query 112. The model can be, for example, a word embedding model.

The text embedder unit 104 can employ various techniques to derive a context of the query 112. The text embedder unit 104 can organize the query 112 into a parse tree to assist in determining the context. The text embedder unit 104 can parse the query 112 through various methods, for example, a constituency parsing method. A constituency parsing method involves reconstructing a query into a constituency-based parse tree describing the passage's syntactic structure based on a phase structure grammar. Phase structure grammar is based upon constituency relations between tokens as opposed to dependency relations between tokens. The text embedder unit 104 can also employ a dependency parsing method, in which a parse tree is constructed based on a dependency relation between tokens. Although only two methods are described, the text embedder unit 104 can employ various methods to organize a query 112 into a parse tree. The text embedder unit 104 can rely on the organization of the tokens in the text tree to determine a context of the query 112. This can be based on words surrounding a target word in the query, or using a target word to derive the meaning of the surrounding words. Upon determining a context, the text embedder unit 104 can generate a user text embedding vector. The user text embedding vector is a numeric representation of the respective words and phrases in the query 112 and denotes the query's semantic meaning.

The multi-modal encoder unit 106 is operable to determine a correlation between the user text embedding vector and the user image embedding vector. The multi-modal encoder unit 106 can map tokens described by the user text embedding vector to features in the user image embedding vector. The mapping helps enrich a contextual understanding of the query 112. Therefore, if the query 112 is "Should I be concerned with this?", there would be mapping to an object in the image 110 and it can be determined that "this" is in reference to the object, for example, a femur. The multi-modal encoder unit 106 is operable to generate a user joint representation of the user text embedding vector and the user image embedding vector. This multi-modal encoder unit 106 can translate the user joint representation to the same common embedding space as the image-text representation 500. The user joint representation can be in the form of a high-dimensional vector.

The answer unit 108 can generate an answer to the query 112. The answer unit 108 generates an answer token by token based at least in part on the user joint representation and the image-text representation 500. In some embodiments of the present invention, the answer unit 108 can alter the image 110 to highlight a target object of the query 112. The answer unit 108 can select an object based on the user joint representation to determine. The answer unit 108 can further visually alter the object for highlighting purposes on a user's graphical user interface. For example, the answer unit 108 can alter the image pixels to change a color of the object, add a border to the object alter the image pixels of the balance of the image 110 (e.g., blur the rest of the image 110). This allows a potential user to feel confident that a generated answer is in response to the query 112.

In embodiments of the present invention, the answer unit can further alter image pixels of objects related to the query 112, but not the target of the query 112. If in the event that a related object is not detected in the image 110, the answer unit 108 can retrieved and image of the object from a database and provide an image of the related object via the graphical user interface. For example, a query 112 may be targeted to an image of a liver suffering from hepatic encephalopathy (HE). HE can affect the functioning of the nervous system and the brain. The answer unit 108 can be trained to recognize related effects of a condition. In this situation, the answer unit 108 can determine whether either a nervous system is in the image 110. If so, the answer unit 108 can alter the nervous system image for highlighting purposes. The highlighting can be distinct from the liver highlighting. If the nervous system is not detected in the image 110, the answer unit 108 can retrieve an image of a nervous system and provide an image to the user. The retrieved nervous system image can include the effects of the HE. In this sense, both a medical student and a health care professional receive information regarding related issues.

As used herein, "machine learning" broadly describes a function of electronic systems that learn from data. A machine learning system, engine, or module can include a machine learning algorithm that can be trained, such as in an external cloud environment (e.g., the cloud computing environment 50), to learn functional relationships between inputs and outputs that are currently unknown. In one or more embodiments, machine learning functionality can be implemented using an artificial neural network (ANN), having the capability to be trained to perform a currently unknown function. In machine learning and cognitive science, ANNs are a family of statistical learning models inspired by the biological neural networks of animals, and in particular, the brain. ANNs can be used to estimate or approximate systems and functions that depend on a large number of inputs.

ANNs can be embodied as so-called "neuromorphic" systems of interconnected processor elements that act as simulated "neurons" and exchange "messages" between each other in the form of electronic signals. Similar to the so-called "plasticity" of synaptic neurotransmitter connections that carry messages between biological neurons, the connections in ANNs that carry electronic messages between simulated neurons are provided with numeric weights that correspond to the strength or weakness of a given connection. The weights can be adjusted and tuned based on experience, making ANNs adaptive to inputs and capable of learning. For example, an ANN for handwriting recognition is defined by a set of input neurons that can be activated by the pixels of an input image. After being weighted and transformed by a function determined by the network's designer, the activation of these input neurons is then passed to other downstream neurons, which are often referred to as "hidden" neurons. This process is repeated until an output neuron is activated. The activated output neuron determines which character was read.

Figure 6:
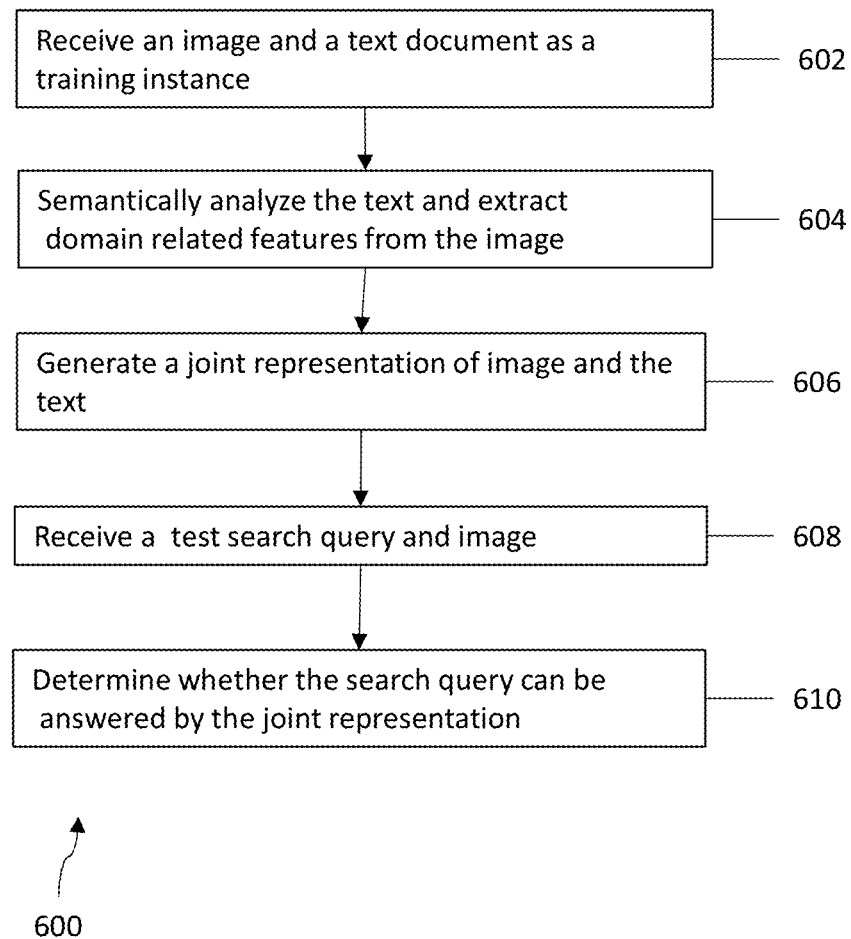
FIG. 6 illustrates a flow diagram of a process for training a visual question answering system in accordance with one or more embodiments of the present invention.

Referring to FIG. 6, a process 600 for training a visual question answering system in accordance with one or more embodiments of the present invention is shown. It should be appreciated that all or a portion of the processing shown in FIG. 6 can be performed by a computer system, such as system 100 of FIG. 5. At block 602, an image embedder unit 102 can receive a digital image 202 and a text embedder unit 104 can receive an electronic text document 206 as training instances. The text document 206 can describe an object(s) in the image 202. In some embodiments of the present invention, the image 202 is a medical image, and the text document 206 is a medical report describing an object in the image.

At block 604, the image embedder unit 102 can be trained to extract domain-related features from the image. In some embodiments of the present invention, the image embedder unit 102 can be implemented by a neural network. The neural network can execute a model to extract features and classify objects in the image 202. During a training phase, the weights and biases of the neural network can be adjusted to cause the model to extract and classify healthcare related objects. The image embedder unit 102 can further generate an image embedding vector 204 based on the weights and biases. Additionally, the text embedder unit 104 can semantically analyze the text document 206. In some embodiments of the present invention, the text embedder unit 104 can also be implemented by a neural network. The neural network can execute a model that applies natural language processing techniques to determine a semantic meaning of the text document 206. During a training phase, the weights and biases of the neural network can be adjusted to cause the model to recognize a healthcare related meaning of the text document 206. The text embedder unit 104 can further generate a text embedding vector 208 based on the weights and biases.

At block 606, a multi-modal encoder unit 106 can receive the image embedding vector 204 and the text embedding vector 208. In some embodiments of the present invention, the multi-modal encoder unit 106 can be implemented by a neural network that executes a model. During a training phase, the weights and biases of the neural network can be adjusted to cause the model to determine a correlation between an object in the image 202 and a natural language description in the text document 206. The multi-modal encoder unit 106 can write data structure to the image embedding vector 204 and the text embedding vector 208 to generate a mapping between the features of the image 202 and the respective portions of the text document 206 that describe the features. The data structure can be, for example, an mapping. For example, the multi-modal encoder unit 106 can write an function that associates a first portion of the image embedding vector 204 to a portion of the text embedding vector 208. The multi-modal encoder unit 106 can further use the mapping to generate a joint image-text representation 500 of the image 202 and the text document.

At block 608, an answer unit 108 can receive an image 110 and a query 112 related to the image. In some embodiments of the present invention, the answer unit 108 can be implemented by a neural network that executes a model. The answer unit 108 can be trained to classify objects in the image 110, and generate a user image embedding vector. The answer unit 108 can further be trained to semantically analyze the query 112 and determine which object(s) in the image 110 is the query 112 referring to. The answer unit 108 can further generate a user text embedding vector. The answer unit 108 can map the user text embedding vector to the object being referred to in the image 110. Based on the mapping, the answer unit 108 can generate a joint user text-image representation. The joint user image-text representation can be translated to a same space as the joint image-text representation 500.

At block 610, the answer unit 108 can determine whether the joint image-text representation 500 references an answer to the query 112. In some embodiments of the present invention, both the joint user image-text representation and the joint image-text representation 500 can be in the form of respective vectors that relate to a semantic meaning of each. The answer unit 108 can determine whether the joint user image-text representation and the joint image-text representation 500 are within a threshold distance of each other. If the joint user image-text representation and the joint image-text representation 500 are within a threshold distance, the answer unit 108 can extract a natural language answer from the textual portion of the joint image-text representation 500. The answer unit 108 can further display the answer on the user computing device 114. If the joint user image-text representation and the joint image-text representation 500 are not within a threshold distance, the answer unit 108 can compare a distance between the joint user image-text representation another the joint image-text representation.

It is to be understood that although this disclosure includes a detailed description on cloud computing, implementation of the teachings recited herein are not limited to a cloud computing environment. Rather, embodiments of the present invention are capable of being implemented in conjunction with any other type of computing environment now known or later developed.

Cloud computing is a model of service delivery for enabling convenient, on-demand network access to a shared pool of configurable computing resources (e.g., networks, network bandwidth, servers, processing, memory, storage, applications, virtual machines, and services) that can be rapidly provisioned and released with minimal management effort or interaction with a provider of the service. This cloud model may include at least five characteristics, at least three service models, and at least four deployment models.

Characteristics are as follows:

On-demand self-service: a cloud consumer can unilaterally provision computing capabilities, such as server time and network storage, as needed automatically without requiring human interaction with the service's provider.

Broad network access: capabilities are available over a network and accessed through standard mechanisms that promote use by heterogeneous thin or thick client platforms (e.g., mobile phones, laptops, and PDAs).

Resource pooling: the provider's computing resources are pooled to serve multiple consumers using a multi-tenant model, with different physical and virtual resources dynamically assigned and reassigned according to demand. There is a sense of location independence in that the consumer generally has no control or knowledge over the exact location of the provided resources but may be able to specify location at a higher level of abstraction (e.g., country, state, or datacenter).

Rapid elasticity: capabilities can be rapidly and elastically provisioned, in some cases automatically, to quickly scale out and rapidly released to quickly scale in. To the consumer, the capabilities available for provisioning often appear to be unlimited and can be purchased in any quantity at any time.

Measured service: cloud systems automatically control and optimize resource use by leveraging a metering capability at some level of abstraction appropriate to the type of service (e.g., storage, processing, bandwidth, and active user accounts). Resource usage can be monitored, controlled, and reported, providing transparency for both the provider and consumer of the utilized service.

Service Models are as follows:

Software as a Service (SaaS): the capability provided to the consumer is to use the provider's applications running on a cloud infrastructure. The applications are accessible from various client devices through a thin client interface such as a web browser (e.g., web-based e-mail). The consumer does not manage or control the underlying cloud infrastructure including network, servers, operating systems, storage, or even individual application capabilities, with the possible exception of limited user-specific application configuration settings.

Platform as a Service (PaaS): the capability provided to the consumer is to deploy onto the cloud infrastructure consumer-created or acquired applications created using programming languages and tools supported by the provider. The consumer does not manage or control the underlying cloud infrastructure including networks, servers, operating systems, or storage, but has control over the deployed applications and possibly application hosting environment configurations.

Infrastructure as a Service (IaaS): the capability provided to the consumer is to provision processing, storage, networks, and other fundamental computing resources where the consumer is able to deploy and run arbitrary software, which can include operating systems and applications. The consumer does not manage or control the underlying cloud infrastructure but has control over operating systems, storage, deployed applications, and possibly limited control of select networking components (e.g., host firewalls).

Deployment Models are as follows:

Private cloud: the cloud infrastructure is operated solely for an organization. It may be managed by the organization or a third party and may exist on-premises or off-premises.

Community cloud: the cloud infrastructure is shared by several organizations and supports a specific community that has shared concerns (e.g., mission, security requirements, policy, and compliance considerations). It may be managed by the organizations or a third party and may exist on-premises or off-premises.

Public cloud: the cloud infrastructure is made available to the general public or a large industry group and is owned by an organization selling cloud services.

Hybrid cloud: the cloud infrastructure is a composition of two or more clouds (private, community, or public) that remain unique entities but are bound together by standardized or proprietary technology that enables data and application portability (e.g., cloud bursting for load-balancing between clouds).

A cloud computing environment is service oriented with a focus on statelessness, low coupling, modularity, and semantic interoperability. At the heart of cloud computing is an infrastructure that includes a network of interconnected nodes.

Figure 7:
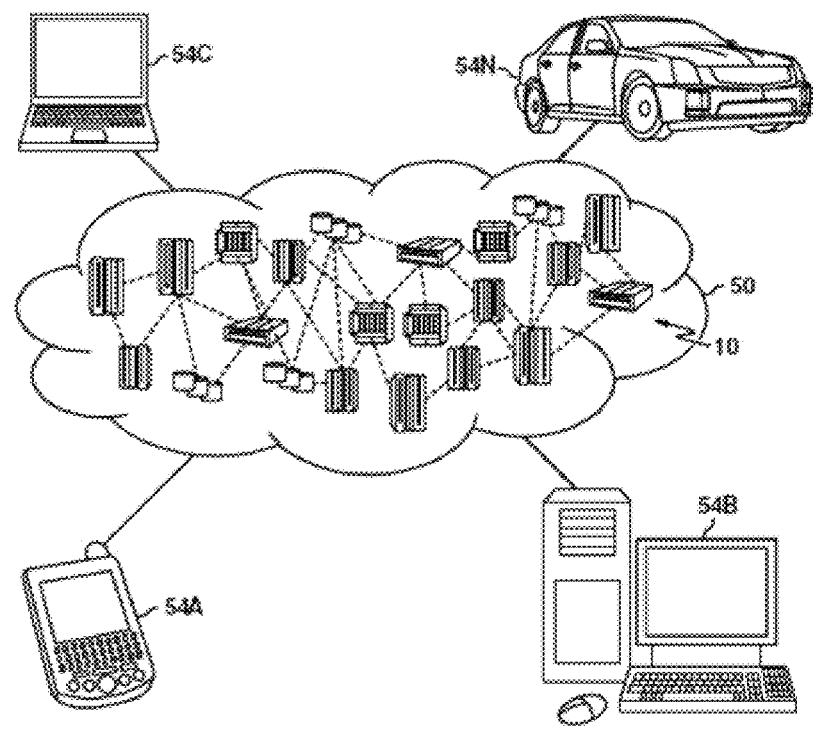
FIG. 7 illustrates a cloud computing environment according to one or more embodiments of the present invention.

Referring now to FIG. 7, illustrative cloud computing environment 50 is depicted. As shown, cloud computing environment 50 includes one or more cloud computing nodes 10 with which local computing devices used by cloud consumers, such as, for example, personal digital assistant (PDA) or cellular telephone 54A, desktop computer 54B, laptop computer 54C, and/or automobile computer system 54N may communicate. Nodes 10 may communicate with one another. They may be grouped (not shown) physically or virtually, in one or more networks, such as Private, Community, Public, or Hybrid clouds as described hereinabove, or a combination thereof. This allows cloud computing environment 50 to offer infrastructure, platforms and/or software as services for which a cloud consumer does not need to maintain resources on a local computing device. It is understood that the types of computing devices 54A-N shown in FIG. 7 are intended to be illustrative only and that computing nodes 10 and cloud computing environment 50 can communicate with any type of computerized device over any type of network and/or network addressable connection (e.g., using a web browser).

Figure 8:
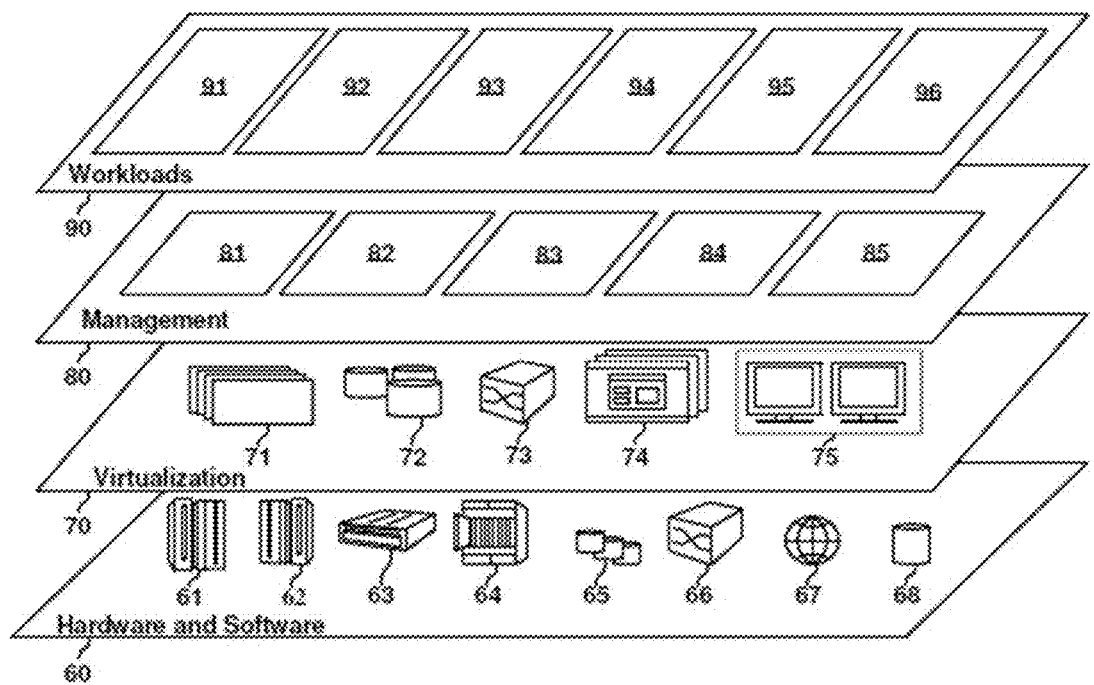
FIG. 8 illustrates abstraction model layers according to one or more embodiments of the present invention.

Referring now to FIG. 8, a set of functional abstraction layers provided by cloud computing environment 50 (FIG. 7) is shown. It should be understood in advance that the components, layers, and functions shown in FIG. 8 are intended to be illustrative only and embodiments of the invention are not limited thereto. As depicted, the following layers and corresponding functions are provided:

Hardware and software layer 60 includes hardware and software components. Examples of hardware components include: mainframes 61; RISC (Reduced Instruction Set Computer) architecture based servers 62; servers 63; blade servers 64; storage devices 65; and networks and networking components 66. In some embodiments, software components include network application server software 67 and database software 68.

Virtualization layer 70 provides an abstraction layer from which the following examples of virtual entities may be provided: virtual servers 71; virtual storage 72; virtual networks 73, including virtual private networks; virtual applications and operating systems 74; and virtual clients 75.

In one example, management layer 80 may provide the functions described below. Resource provisioning 81 provides dynamic procurement of computing resources and other resources that are utilized to perform tasks within the cloud computing environment. Metering and Pricing 82 provide cost tracking as resources are utilized within the cloud computing environment, and billing or invoicing for consumption of these resources. In one example, these resources may include application software licenses. Security provides identity verification for cloud consumers and tasks, as well as protection for data and other resources. User portal 83 provides access to the cloud computing environment for consumers and system administrators. Service level management 84 provides cloud computing resource allocation and management such that required service levels are met. Service Level Agreement (SLA) planning and fulfillment 85 provide pre-arrangement for, and procurement of, cloud computing resources for which a future requirement is anticipated in accordance with an SLA.

Workloads layer 90 provides examples of functionality for which the cloud computing environment may be utilized. Examples of workloads and functions which may be provided from this layer include: mapping and navigation 91; software development and lifecycle management 92; virtual classroom education delivery 93; data analytics processing 94; transaction processing 95; and visual question answering 96.

Figure 9:
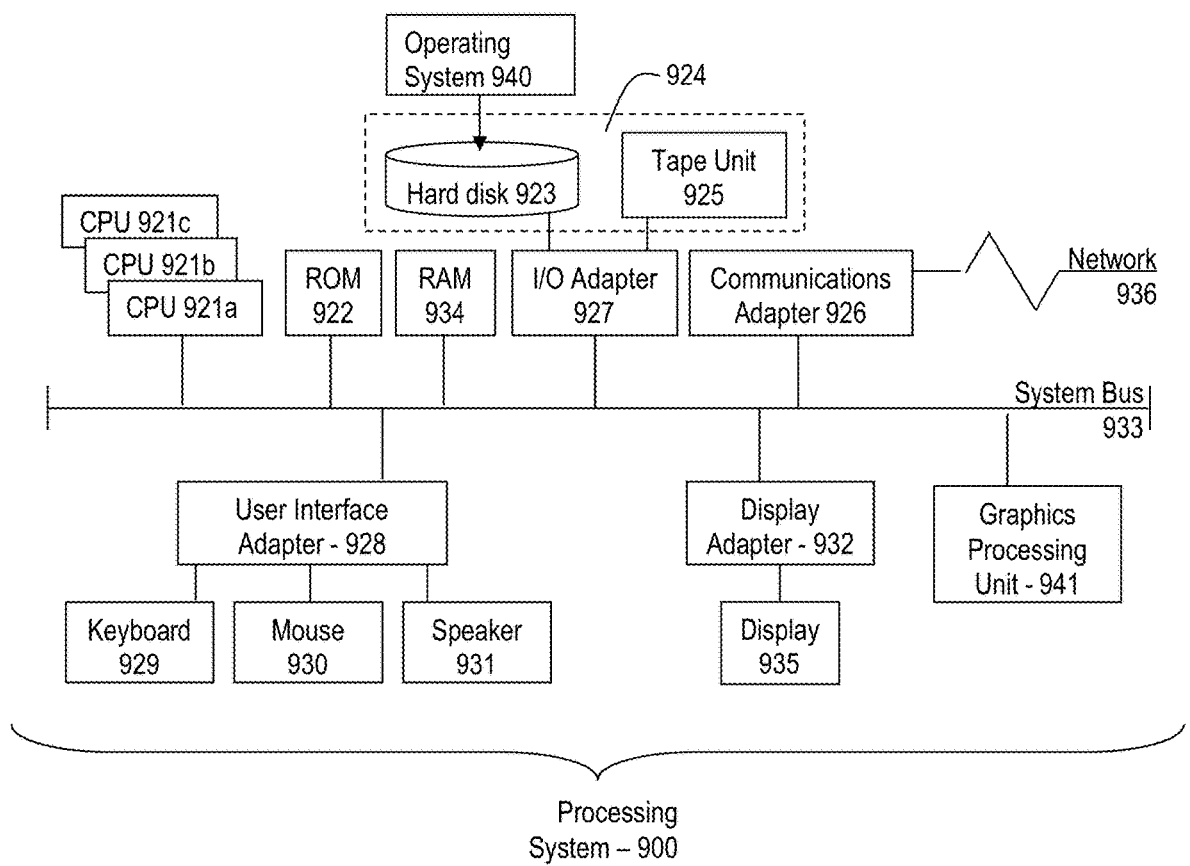
FIG. 9 illustrates a block diagram of a computer system for use in implementing one or more embodiments of the present invention.

It is understood that the present disclosure is capable of being implemented in conjunction with any other type of computing environment now known or later developed. For example, FIG. 9 depicts a block diagram of a processing system 900 for implementing the techniques described herein. In examples, the processing system 900 has one or more central processing units (processors) 921a, 921b, 921c, etc. (collectively or generically referred to as processor(s) 921 and/or as processing device(s)). In aspects of the present disclosure, each processor 921 can include a reduced instruction set computer (RISC) microprocessor. Processors 921 are coupled to system memory (e.g., random access memory (RAM) 924) and various other components via a system bus 933. Read only memory (ROM) 922 is coupled to system bus 933 and may include a basic input/output system (BIOS), which controls certain basic functions of the processing system 900.

Further depicted are an input/output (I/O) adapter 927 and a network adapter 926 coupled to the system bus 933. I/O adapter 927 may be a small computer system interface (SCSI) adapter that communicates with a hard disk 923 and/or a storage device 925 or any other similar component. I/O adapter 927, hard disk 923, and storage device 925 are collectively referred to herein as mass storage 934. Operating system 940 for execution on processing system 900 may be stored in mass storage 934. The network adapter 926 interconnects system bus 933 with an outside network 936 enabling processing system 900 to communicate with other such systems.

A display (e.g., a display monitor) 935 is connected to the system bus 933 by display adapter 932, which may include a graphics adapter to improve the performance of graphics intensive applications and a video controller. In one aspect of the present disclosure, adapters 926, 927, and/or 932 may be connected to one or more I/O busses that are connected to the system bus 933 via an intermediate bus bridge (not shown). Suitable I/O buses for connecting peripheral devices such as hard disk controllers, network adapters, and graphics adapters typically include common protocols, such as the Peripheral Component Interconnect (PCI). Additional input/output devices are shown as connected to system bus 933 via user interface adapter 928 and display adapter 932. An input device 929 (e.g., a keyboard, a microphone, a touchscreen, etc.), an input pointer 930 (e.g., a mouse, trackpad, touchscreen, etc.), and/or a speaker 931 may be interconnected to system bus 933 via user interface adapter 928, which may include, for example, a Super I/O chip integrating multiple device adapters into a single integrated circuit.

In some aspects of the present disclosure, the processing system 900 includes a graphics processing unit 937. Graphics processing unit 937 is a specialized electronic circuit designed to manipulate and alter memory to accelerate the creation of images in a frame buffer intended for output to a display. In general, graphics processing unit 937 is very efficient at manipulating computer graphics and image processing and has a highly parallel structure that makes it more effective than general-purpose CPUs for algorithms where processing of large blocks of data is done in parallel.

Thus, as configured herein, the processing system 900 includes processing capability in the form of processors 921, storage capability including system memory (e.g., RAM 929), and mass storage 934, input means such as keyboard 929 and mouse 930, and output capability including speaker 931 and display 935. In some aspects of the present disclosure, a portion of system memory (e.g., RAM 924) and mass storage 934 collectively store the operating system 940 to coordinate the functions of the various components shown in the processing system 900.

Various embodiments of the invention are described herein with reference to the related drawings. Alternative embodiments of the invention can be devised without departing from the scope of this invention. Various connections and positional relationships (e.g., over, below, adjacent, etc.) are set forth between elements in the following description and in the drawings. These connections and/or positional relationships, unless specified otherwise, can be direct or indirect, and the present invention is not intended to be limiting in this respect. Accordingly, a coupling of entities can refer to either a direct or an indirect coupling, and a positional relationship between entities can be a direct or indirect positional relationship. Moreover, the various tasks and process steps described herein can be incorporated into a more comprehensive procedure or process having additional steps or functionality not described in detail herein.

One or more of the methods described herein can be implemented with any or a combination of the following technologies, which are each well known in the art: a discrete logic circuit(s) having logic gates for implementing logic functions upon data signals, an application specific integrated circuit (ASIC) having appropriate combinational logic gates, a programmable gate array(s) (PGA), a field programmable gate array (FPGA), etc.

For the sake of brevity, conventional techniques related to making and using aspects of the invention may or may not be described in detail herein. In particular, various aspects of computing systems and specific computer programs to implement the various technical features described herein are well known. Accordingly, in the interest of brevity, many conventional implementation details are only mentioned briefly herein or are omitted entirely without providing the well-known system and/or process details.

In some embodiments, various functions or acts can take place at a given location and/or in connection with the operation of one or more apparatuses or systems. In some embodiments, a portion of a given function or act can be performed at a first device or location, and the remainder of the function or act can be performed at one or more additional devices or locations.

The terminology used herein is for the purpose of describing particular embodiments only and is not intended to be limiting. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, element components, and/or groups thereof.

The corresponding structures, materials, acts, and equivalents of all means or step plus function elements in the claims below are intended to include any structure, material, or act for performing the function in combination with other claimed elements as specifically claimed. The present disclosure has been presented for purposes of illustration and description, but is not intended to be exhaustive or limited to the form disclosed. Many modifications and variations will be apparent to those of ordinary skill in the art without departing from the scope and spirit of the disclosure. The embodiments were chosen and described in order to best explain the principles of the disclosure and the practical application, and to enable others of ordinary skill in the art to understand the disclosure for various embodiments with various modifications as are suited to the particular use contemplated.

The diagrams depicted herein are illustrative. There can be many variations to the diagram or the steps (or operations) described therein without departing from the spirit of the disclosure. For instance, the actions can be performed in a differing order or actions can be added, deleted or modified. Also, the term "coupled" describes having a signal path between two elements and does not imply a direct connection between the elements with no intervening elements/ connections therebetween. All of these variations are considered a part of the present disclosure.

The following definitions and abbreviations are to be used for the interpretation of the claims and the specification. As used herein, the terms "comprises," "comprising," "includes," "including," "has," "having," "contains" or "containing," or any other variation thereof, are intended to cover a non-exclusive inclusion. For example, a composition, a mixture, process, method, article, or apparatus that comprises a list of elements is not necessarily limited to only those elements but can include other elements not expressly listed or inherent to such composition, mixture, process, method, article, or apparatus.

Additionally, the term "exemplary" is used herein to mean "serving as an example, instance or illustration." Any embodiment or design described herein as "exemplary" is not necessarily to be construed as preferred or advantageous over other embodiments or designs. The terms "at least one" and "one or more" are understood to include any integer number greater than or equal to one, i.e. one, two, three, four, etc. The terms "a plurality" are understood to include any integer number greater than or equal to two, i.e. two, three, four, five, etc. The term "connection" can include both an indirect "connection" and a direct "connection."

The terms "about," "substantially," "approximately," and variations thereof, are intended to include the degree of error associated with measurement of the particular quantity based upon the equipment available at the time of filing the application. For example, "about" can include a range of ±8% or 5%, or 2% of a given value.

The present invention may be a system, a method, and/or a computer program product at any possible technical detail level of integration. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punchcards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, configuration data for integrated circuitry, or either source code or object code written in any combination of one or more programming languages, including an object oriented programming language such as Smalltalk, C++, or the like, and procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instruction by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the blocks may occur out of the order noted in the Figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

The descriptions of the various embodiments of the present invention have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments described herein.

What is claimed is:

1. A computer-implemented method comprising:
    extracting, by a processor, a domain-specific object feature from a first image data, wherein the feature describes an object in the first image data;
    determining, by the processor, domain-specific semantic meaning of text data;
    mapping, by the processor, the object feature to a portion of the text data, wherein the portion of the text data describes the object;
    creating, by the processor, a joint representation of the object and the portion of the text data;
    receiving, by the processor, a second image data and a query directed towards an object in the second image data; and
    generating, by the processor, an answer to the query based on the joint representation.

2. The computer-implemented method of claim 1, wherein extracting the domain-specific object feature comprises:
    generating a bounding box around the object in the first image data; and
    extracting the object feature from within the bounding box.

3. The computer-implemented method of claim 1, wherein determining the domain-specific semantic meaning comprises:
    organizing the text data into a parse tree, wherein the parse tree is segmented into tokens;
    masking a token of the segmented tokens in the parse tree; and determining a semantic meaning of the masked token based at least in part on tokens surrounding the masked token.

4. The computer-implemented method of claim 1 further comprising:
providing a training image and a training query;
determining an object in the training image associated with the training query; and
generating a natural language response to the training query based on the joint representation.

5. The computer-implemented method of claim 4 further comprising displaying the natural language response on a display of a user computing device.

6. The computer-implemented method of claim 1, wherein the domain-specific object feature are extracted by a region-based convolutional neural network (R-CNN) and the semantic meaning is determined by a recurrent neural network (RNN).

7. The computer-implemented method of claim 1, wherein the first image data and the text data are related to a healthcare domain.

8. A system comprising:
a memory having computer readable instructions; and
one or more processors for executing the computer readable instructions, the computer readable instructions controlling the one or more processors to perform operations comprising:
extracting a domain-specific object feature from a first image data, wherein the feature describes an object in the first image data;
determining domain-specific semantic meaning of text data;
mapping the object feature to a portion of the text data, wherein the portion of the text data describes the object;
creating a joint representation of the object and the portion of the text data;
receiving a second image data and a query directed towards an object in the second image data; and
generating, by the processor, an answer to the query based on the joint representation.

9. The system of claim 8, wherein extracting the domain-specific object feature comprises:
generating a bounding box around the object in the first image data; and
extracting the object feature from within the bounding box.

10. The system of claim 8, wherein determining the domain-specific semantic meaning comprises:
organizing the text data into a parse tree, wherein the parse tree is segmented into tokens;
masking a token of the segmented tokens in the parse tree from at least one layer of the neural network; and
determining a semantic meaning of the masked token based at least in part on tokens surrounding the masked token.

11. The system of claim 8, the operations further comprising:
providing the neural network with a training image and a training query;
determining an object in the training image associated with the training query; and
generating a natural language response to the training query based on the joint representation.

12. The system of claim 11, the operations further comprising displaying the natural language response on a display of a user computing device.

13. The system of claim 8, wherein the domain-specific object feature are extracted by a region-based convolutional neural network (R-CNN) and the semantic meaning is determined by a recurrent neural network (RNN).

14. The system of claim 8, wherein the first image data and the text data are related to a healthcare domain.

15. A computer program product comprising a computer readable storage medium having program instructions embodied therewith, the program instructions executable by a processor of a neural network to cause the processor to perform operations comprising:
extracting a domain-specific object feature from a first image data, wherein the feature describes an object in the first image data;
determining domain-specific semantic meaning of text data;
mapping the object feature to a portion of the text data, wherein the portion of the text data describes the object;
creating a joint representation of the object and the portion of the text data;
receiving a second image data and a query directed towards an object in the second image data; and
generating, by the processor, an answer to the query based on the joint representation.

16. The computer program product of claim 15, wherein extracting the domain-specific object feature comprises:
generating a bounding box around the object in the first image data; and
extracting the object feature from within the bounding box.

17. The computer program product of claim 15, wherein determining the domain-specific semantic meaning comprises:
organizing the text data into a parse tree, wherein the parse tree is segmented into tokens;
masking a token of the segmented tokens in the parse tree from at least one layer of the neural network; and
determining a semantic meaning of the masked token based at least in part on tokens surrounding the masked token.

18. The computer program product of claim 15, the operations further comprising:
providing the neural network with a training image and a training query;
determining an object in the training image associated with the training query; and
generating a natural language response to the training query based on the joint representation.

19. The computer program product of claim 18, the operations further comprising displaying the natural language response on a display of a user computing device.

20. The computer program product of claim 15, wherein the domain-specific object feature are extracted by a region-based convolutional neural network (R-CNN) and the semantic meaning is determined by a recurrent neural network (RNN).

* * * * *